US011890401B2

(12) United States Patent
Jeppsson et al.

(10) Patent No.: US 11,890,401 B2
(45) Date of Patent: *Feb. 6, 2024

(54) DIALYSIS MACHINES AND METHODS OF DISINFECTING A DIALYSIS MACHINE

(71) Applicant: GAMBRO LUNDIA AB, Lund (SE)

(72) Inventors: Helena Jeppsson, Hörby (SE); Jan Sternby, Lund (SE); Thomas Hertz, Lund (SE); Olof Jansson, Vellinge (SE); Sture Hobro, Lund (SE); Evi Martinson, Södra Sandby (SE)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/679,822

(22) Filed: Feb. 24, 2022

(65) Prior Publication Data

US 2023/0001062 A1 Jan. 5, 2023

Related U.S. Application Data

(63) Continuation of application No. 16/754,160, filed as application No. PCT/EP2017/075930 on Oct. 11, 2017, now Pat. No. 11,260,154.

(51) Int. Cl.
*A61M 1/16* (2006.01)

(52) U.S. Cl.
CPC .......... *A61M 1/1688* (2014.02); *A61M 1/165* (2014.02); *A61M 1/169* (2013.01); *A61M 1/1662* (2014.02)

(58) Field of Classification Search
CPC .. A61M 1/1688; A61M 1/165; A61M 1/1662; A61M 1/169
See application file for complete search history.

(56) References Cited

U.S. PATENT DOCUMENTS

| 3,738,382 A | 6/1973 | Cappelen, Jr. et al. |
| 9,440,015 B2 | 9/2016 | Ritter et al. |

(Continued)

FOREIGN PATENT DOCUMENTS

| JP | 2003310749 | 11/2003 |
| WO | 96/09080 A1 | 3/1996 |

(Continued)

OTHER PUBLICATIONS

International Search Report from International Patent Application No. PCT/EP2017/075930, dated May 30, 2018 (3 Pages).

(Continued)

*Primary Examiner* — Krishnan S Menon
(74) *Attorney, Agent, or Firm* — K&L Gates LLP

(57) ABSTRACT

Dialysis machines comprising a feed arrangement to supply a dialysis fluid to a dialyzer during dialysis treatment and a return arrangement to remove the dialysis fluid from the dialyzer during dialysis treatment and forward it to an exit; a feed recirculation circuit to allow a fluid of the feed arrangement to be re-circulated in a fluid loop path comprising, at least a portion of, the feed arrangement and the feed recirculation circuit and a return recirculation circuit to allow a fluid of the return arrangement to re-circulate in an auxiliary fluid loop path comprising, at least a portion of, the return arrangement and the return recirculation circuit. A controller configured to perform disinfection by re-circulating a disinfectant and/or a heated fluid through said fluid loop path and/or through said auxiliary fluid loop path. The dialysis machine further comprises a feed forward arrangement connected to the fluid loop path and arranged to enable a fluid of the feed arrangement to be forwarded to the exit by-passing the auxiliary fluid loop path.

26 Claims, 6 Drawing Sheets

(56) References Cited

U.S. PATENT DOCUMENTS

2011/0300230 A1 12/2011 Peterson et al.
2014/0217020 A1 8/2014 Meyer et al.
2016/0256582 A1 9/2016 Hertz et al.

FOREIGN PATENT DOCUMENTS

WO 96/40314 A1 12/1996
WO 2015/071244 A1 5/2015

OTHER PUBLICATIONS

Written Opinion from International Patent Application No. PCT/EP2017/075930, dated May 30, 2018 (8 Pages).

DIALYSIS MACHINES AND METHODS OF DISINFECTING A DIALYSIS MACHINE

PRIORITY CLAIM

The present application is a continuation of U.S. application Ser. No. 16/754,160, filed Apr. 7, 2020, now U.S. Pat. No. 11,260,154, which is a national stage entry of WIPO Application No. PCT/EP2017/075930, filed Oct. 11, 2017. The entire contents of each are herein incorporated by reference and relied upon.

TECHNICAL FIELD

The present invention relates to dialysis machines capable of commencing treatment fluid preparation and/or distribution at the same time as other parts of the fluid path is being disinfected. The invention also relates to a method of disinfecting a dialysis machine.

BACKGROUND

There are several types of treatments in which blood is extracted in an extracorporeal blood circuit. Such treatments involve, for example, haemodialysis, haemofiltration, haemodiafiltration, plasmapheresis, etc. Normally, blood is removed from a blood vessel at an access site and returned to the same blood vessel or at another location.

In for example the cases of haemodialysis, haemofiltration, haemodiafiltration, and plasmapheres, but not limited to these cases, a treatment fluid (also referred to as a dialysis fluid) is made approximately isotonic with a patient's blood. In haemodialysis and haemodiafiltration, the treatment fluid and the patient's blood are made to flow on each side of a semi-permeable membrane of a membrane device (referred to as a dialyzer). Diffusive transfer is achieved from one side of the membrane to the other when the concentration of the substance on each side of the membrane differs. Such substances may be impurities in the blood (urea, creatinine, etc.) which thereby migrates from the blood to the treatment fluid. Since fluid normally has to be removed from the patient during haemodialysis, a convective transfer by ultrafiltration, resulting from a pressure difference created between the blood side and the treatment fluid side of the membrane, is added to the diffusive transfer.

An apparatus for extracorporeal blood treatment includes a dialysis machine which is connected to a disposable extracorporeal blood circuit. The disposable extracorporeal blood circuit includes blood transport lines (in general an arterial line for blood removal from the patient, and a venous line for blood return to the patient) and the membrane device for blood treatment.

The semi-permeable membrane of the membrane device divides a blood compartment, connected to the blood transport lines, and a fluid compartment, connected to treatment fluid supply and discharge circuits. The blood transport lines are further coupled to a sensor and actuator system equipped on the dialysis machine, which system normally comprises means for blood circulation, pressure sensors, air bubble sensor, one or more circuit blocking clamps, blood detector, etc.

The treatment fluid supply circuit receives purified water from a water supply system. The water supply system may be a small unit providing water to only a single treatment control machine, but may also be a large unit providing water by means of a water system loop arrangement to a significant number of treatment units in for example a hospital or a clinic.

Dialysis fluid, which may come into contact with the patients' blood, is often prepared from the purified water by means of a treatment fluid supply circuit. It is of paramount importance that the dialysis fluid used for the treatment is substantially free from virus, fungi, bacteria and their residue and degradation products, such as endotoxins.

Therefore, the treatment fluid path of a dialysis machine may be disinfected between dialysis treatments in order to reduce the presence of virus, fungi, bacteria, etc in the treatment fluid path. Chemical disinfection (e.g. using NaOCl or other chemical disinfection agents) is an efficient way to reduce the presence of bacteria, etc but it makes great demands on the following rinse procedure and requires very close measuring to assure that the treatment fluid path is free of chemical residual products before being used for subsequent treatments. The chemical process is not environmentally friendly and may have a negative effect on the life-length of the disinfected parts and components.

In an alternative disinfection process, thermal disinfection is achieved by letting hot water pass through the treatment fluid path. As a result, the problem of chemical residual products does not exist, the process puts less load on the environment, and often has comparatively less negative effect on the life-length of the disinfected parts and components compared to the use of biological aggressive solutions (as for example Chlorine).

In a further alternative disinfection process, the thermal disinfection is combined with chemical agents, such as citric acid, in order to achieve an efficient disinfection of the treatment fluid path.

WO96/09080 discloses a disinfection arrangement for a dialysis machine consisting of a clean side and dirty side. The clean side comprises an inlet for water, a heat exchanger as well as a water vessel containing a heater. A feed conduit leads from the water vessel to a tube which is normally connected to the clean side of the dialyser but, during disinfection, is connected to a recirculation conduit via a valve in order to perform a first recirculation circuit. A second recirculation circuit is constituted by a recirculation conduit, a valve, a tube, which is normally connected to the dirty side of a dialyser, a return conduit as well as a pump. A heat exchanger heats up the fluid in the second circuit with help of the fluid in the first circuit, which is heated up by the heater in the water vessel. A small amount of fluid is transferred from the first circuit to the second circuit via a shunt conduit.

Another example of disinfection arrangement of similar configuration is disclosed in WO96/40314.

Thermal disinfection of the treatment fluid path of a machine is preferably carried out after the treatment of each patient. As the number of dialysis patients increases there is a need to increase the available time for treatments in the clinics. Consequently, there is a desire to reduce the time spent on disinfection between treatments.

Before dialysis treatment can be commenced for a patient, the dialysis machine needs a certain time to start up the production of treatment fluid with the correct composition and at a set temperature. Again, as the number of dialysis patients increases there is a need to increase the available time for treatments in the clinics. Consequently, there is a need to reduce the time spent on the starting-up of the preparation of the treatment fluid before the dialysis treatment can be commenced on the patient.

SUMMARY

According to a first independent aspect of the present invention, there is provided a dialysis machine having a feed arrangement arranged to supply a dialysis fluid to a dialyzer during dialysis treatment; a return arrangement arranged to remove the dialysis fluid from the dialyzer during dialysis treatment and forward it to an exit, in particular said exit being in a portion of the return arrangement external to the fluid loop path and in detail being placed downstream the return circulation circuit with respect to a fluid flow circulation in the return arrangement during dialysis treatment and being adapted for connection to a waste-bag or drain; a return recirculation circuit connected to the return arrangement and arranged to allow a fluid of the return arrangement to re-circulate in a fluid loop path comprising, at least a portion of, the return arrangement and the return recirculation circuit; a controller configured to perform disinfection of the feed arrangement and/or of the return arrangement by circulating a disinfectant and/or a heated fluid through said feed arrangement and/or return arrangement; the dialysis machine further comprises a feed forward arrangement arranged to enable a fluid of the feed arrangement to be forwarded to a waste bag or drain, in particular to said exit, by-passing the fluid loop path.

In the present text, by disinfection is intended cleansing techniques that destroy or prevent growth of microorganisms or their toxins or vectors by exposure to chemical or physical agents, but also the mere cleaning of certain portions of the lines, and/or the decalcification of line tracts.

Moreover, the waste bag or drain to which the feed forward arrangement may forward the fluid may be (or may be not) the same as the waste bag or drain to which said exit is connected (i.e. there might be only one waste bag or drain or two different waste bags or drains).

According to another aspect of the present invention, there is provided a dialysis machine having a feed arrangement arranged to supply a dialysis fluid to a dialyzer during dialysis treatment; a return arrangement arranged to remove the dialysis fluid from the dialyzer during dialysis treatment and forward it to an exit, said exit being adapted for connection to a waste-bag or drain; a feed forward arrangement connected to the feed arrangement and arranged to enable a fluid of the feed arrangement to be forwarded to the exit at the same time as at least a portion of the return arrangement contains a second fluid.

According to another aspect of the present invention, there is provided a dialysis machine having a feed arrangement arranged to supply a dialysis fluid to a dialyzer during dialysis treatment; a return arrangement arranged to remove the dialysis fluid from the dialyzer during dialysis treatment and forward it to an exit, said exit being adapted for connection to a waste-bag or drain; a return recirculation circuit connected to the return arrangement and arranged to allow a second fluid to circulate in a fluid path comprising, at least a portion of, the return arrangement and the return recirculation circuit; a feed forward arrangement connected to the feed arrangement and arranged to enable a third fluid of the feed arrangement to be forwarded to the exit at the same time as the second fluid is being circulated in at least a portion of the return arrangement and the return recirculation circuit.

In a $1^{st}$ depending aspect according to previous aspects, the dialysis machine comprises a return recirculation circuit connected to the return arrangement and arranged to allow the second fluid to circulate in a fluid path comprising, at least a portion of, the return arrangement and the return recirculation circuit at the same time as a fluid is forwarded from the feed arrangement to the exit by means of the feed forward arrangement.

In a $2^{nd}$ depending aspect according to previous aspect, a feed recirculation circuit is connected to the feed arrangement and arranged to allow a fluid of the feed arrangement to be circulated in a fluid path comprising, at least a portion of, the feed arrangement and the feed recirculation circuit at the same time the second fluid is being circulated in at least a portion of the return arrangement and the return recirculation circuit.

In a $3^{rd}$ depending aspect according to previous aspect, the machine comprises a controller configured to perform disinfection of the feed arrangement and the return arrangement, separately, by circulating a first disinfectant and/or a first heated fluid through at least a portion of said feed arrangement and said feed recirculation circuit and by circulating a second disinfectant and/or a second heated fluid through at least a portion of the return arrangement and said return recirculation circuit.

In a $4^{th}$ depending aspect according to previous aspect, the controller is configured to discontinue the disinfection of the feed arrangement and lead the first disinfectant and/or first heated fluid towards the exit by means of the feed forward arrangement and commencing the preparation of dialysis fluid in the feed arrangement while continuing disinfecting the return arrangement by continuing circulating the second disinfectant and/or second heated fluid through said return recirculation circuit.

In a $5^{th}$ depending aspect according to anyone of the previous aspects, the machine comprises a feed recirculation circuit connected to the feed arrangement and arranged to allow a fluid of the feed arrangement to be re-circulated in an auxiliary fluid loop path comprising, at least a portion of, the feed arrangement and the feed recirculation circuit.

In a $6^{th}$ depending aspect according to previous aspect, the feed forward arrangement is connected to the auxiliary fluid loop path and arranged to enable a fluid of the feed arrangement to be forwarded to the exit without circulating in the fluid loop path.

In a $7^{th}$ depending aspect according to previous aspects 5 or 6, the controller is configured to perform disinfection of the feed arrangement by re-circulating a disinfectant and/or a heated fluid through said auxiliary fluid loop path.

In an $8^{th}$ depending aspect according to anyone of the previous aspects, the controller is configured to perform disinfection of the return arrangement by re-circulating a disinfectant and/or a heated fluid through said fluid loop path.

In a $9^{th}$ depending aspect according to anyone of the previous aspects, the controller is configured to forward a fluid of the feed arrangement to the exit at the same time as at least a portion of the return arrangement contains a second different fluid, for example a heated fluid and/or a disinfectant.

In a $10^{th}$ depending aspect according to anyone of the previous aspects, the controller is configured to perform disinfection of the feed arrangement and/or of the return arrangement separately, by circulating a first disinfectant and/or a first heated fluid through at least a portion of said feed arrangement and by re-circulating a second disinfectant and/or a second heated fluid through said fluid loop path.

In a $11^{th}$ depending aspect according to anyone of the previous aspects, the controller is configured to perform disinfection of the feed arrangement and/or of the return arrangement separately, by circulating a first heated fluid through at least a portion of said feed arrangement, and by re-circulating a second heated fluid through said fluid loop path and wherein the first heated fluid is heated at a temperature, e.g. 70°-85° degrees, lower than the temperature, e.g. 75°-95° degrees, of the second heated fluid.

In a 12$^{th}$ depending aspect according to anyone of the previous aspects, the controller is configured to perform disinfection of the feed arrangement and/or of the return arrangement separately, by circulating a first disinfectant and/or a first heated fluid through at least a portion of said feed arrangement for a first time period, e.g. 3-8 minutes, and by re-circulating a second disinfectant and/or a second heated fluid through said fluid loop path for a second time period, e.g. 10-20 min, wherein the first time period is shorter than the second time period.

In a 13$^{th}$ depending aspect according to previous aspect 10, the machine further comprises a feed recirculation circuit connected to the feed arrangement and arranged to allow a fluid of the feed arrangement to be re-circulated in an auxiliary fluid loop path comprising, at least a portion of, the feed arrangement and the feed recirculation circuit and wherein the controller is configured to perform disinfection of the feed arrangement and/or of the return arrangement separately by re-circulating a first disinfectant and/or a first heated fluid through said auxiliary fluid loop path.

In a 14$^{th}$ depending aspect according to anyone of the previous aspects, the controller is configured to re-circulate the fluid of the return arrangement in the fluid loop path at the same time as the fluid of the feed arrangement is forwarded from the feed arrangement to the exit by means of the feed forward arrangement.

In a 15$^{th}$ depending aspect according to anyone of the previous aspects, the controller is configured to re-circulate the fluid of the return arrangement in the fluid loop path at the same time the fluid of the feed arrangement is re-circulated in the auxiliary fluid loop path.

In a 16$^{th}$ depending aspect according to anyone of the previous aspects, the controller is configured to discontinue the disinfection of the feed arrangement and lead a first disinfectant and/or a first heated fluid used to disinfect the feed arrangement towards the exit by means of the feed forward arrangement and commencing the preparation of dialysis fluid in the feed arrangement.

In a 17$^{th}$ depending aspect according to anyone of the previous aspects, the controller is configured to discontinue the disinfection of the feed arrangement and lead the first disinfectant and/or first heated fluid towards the exit by means of the feed forward arrangement and commencing the preparation of dialysis fluid in the feed arrangement, while continuing disinfecting the return arrangement by continuing re-circulating a second disinfectant and/or second heated fluid through said return recirculation circuit.

In a 18$^{th}$ depending aspect according to anyone of the previous aspects, the feed forward arrangement comprises an exit valve for enabling and preventing, respectively, fluid of the feed arrangement to be lead to the exit through said feed forward arrangement.

In a 19$^{th}$ depending aspect according to anyone of the previous aspects, the return recirculation circuit comprise a valve for enabling and preventing, respectively, the circulation of fluid in, at least a portion of the return arrangement and the return recirculation circuit.

In a 20$^{th}$ depending aspect according to anyone of the previous aspects, the feed recirculation circuit comprises a valve for enabling and preventing, respectively, the circulation of fluid in, at least a portion of, the feed arrangement and the feed recirculation circuit.

In a 21$^{st}$ depending aspect according to anyone of the previous aspects, the machine further comprises at least a heater arranged to heat fluid being circulated in the feed arrangement and/or in the fluid loop path.

In a 22$^{nd}$ depending aspect according to anyone of the previous aspects, the machine further comprises a heat-exchanger with a primary and a secondary side, the heat exchanger being arranged to transfer heat between a fluid circulating in the feed arrangement and a fluid of the fluid loop path, and at least one short-cut arrangement arranged to short-cut the primary and/or the secondary side of the heat-exchanger.

In a 23$^{rd}$ depending aspect according to the previous aspect, the controller is configured to activate the at least one short-cut arrangement, and thereby significantly reduce the heat-transfer between the fluids of the primary and secondary side of the heat-exchanger, while commencing the preparation of dialysis fluid in the feed arrangement while continuing disinfecting the return arrangement by continuing re-circulating disinfectant and/or heated fluid through said fluid loop path.

In a 24$^{th}$ depending aspect according to anyone of the previous aspects, the feed arrangement further comprises a by-pass line directly connecting the feed arrangement and the return arrangement, the by-pass line including a valve for enabling and preventing, respectively, the circulation of fluid in the by-pass line.

In a 25$^{th}$ depending aspect according to the previous aspect, the feed forward arrangement is connected to the by-pass line.

In a 26$^{th}$ depending aspect according to anyone of the previous aspects, the machine further includes a treatment fluid preparation unit comprising a preparation line having one end connected to the feed arrangement, a pump acting on the preparation line and a first concentrate connected to the preparation line, during treatment fluid preparation, the controller driving the pump to infuse a concentrate solution into the fluid circulating in the feed arrangement at an infusion point, the treatment fluid preparation unit further comprising a conductivity sensor downstream the infusion point along a fluid flow direction, the controller receiving a signal from the conductivity sensor and controlling the pump at least based on said signal.

In a 27$^{th}$ depending aspect according to the previous aspect, the treatment fluid preparation unit further comprises a second preparation line having one end connected to the feed arrangement, a second pump acting on the second preparation line and a second concentrate connected to the second preparation line, during treatment fluid preparation, the controller driving the second pump to infuse a concentrate solution into the fluid circulating in the feed arrangement at a second infusion point, the treatment fluid preparation unit further comprising a second conductivity sensor downstream the second infusion point along a fluid flow direction, the controller receiving a signal from the second conductivity sensor (114) and controlling the second pump at least based on said signal.

In a 28$^{th}$ depending aspect according to anyone of the previous aspects, the feed arrangement further comprises removable connector connectable to an inlet of the dialyzer during dialysis treatment, said connector being connectable to the feed recirculation circuit to define the auxiliary fluid loop path.

In a 29$^{th}$ depending aspect according to anyone of the previous aspects, the return arrangement further comprises removable connector connectable to an outlet of the dialyzer during dialysis treatment, said connector being connectable to the return recirculation circuit to define the fluid loop path.

In a 30$^{th}$ depending aspect according to anyone of the previous aspects, the controller is configured to perform disinfection of the fluid loop path either upon request from a user or at the latest after the feed arrangement has been disinfected a predetermined number of times, e.g. 2 to 6, without a fluid loop path disinfection occurred.

According to an independent aspect of the present invention, a method of disinfecting a dialysis machine is provided comprising the steps of: i) providing a disinfectant and/or heated fluid; ii) circulating disinfectant and/or heated fluid in a feed arrangement adapted for, during dialysis treatment, supplying dialysis fluid to a dialyzer; iii) re-circulating a disinfectant and/or heated fluid in a fluid loop path comprising a return arrangement adapted for, during dialysis treatment, receiving used dialysis fluid from a dialyzer; iv) leading disinfectant and/or heated fluid from the feed arrangement towards waste bag or drain, thereby discontinuing the disinfection of the feed arrangement, while continuing circulating disinfectant and/or heated fluid in the fluid loop path; v) commencing the preparation of dialysis fluid in the feed arrangement while continuing circulating disinfectant and/or heated fluid in the fluid loop path.

According to a further aspect of the present invention, a method of disinfecting a dialysis machine comprising the steps of: i) circulating a disinfectant and/or heated fluid in an auxiliary fluid loop path comprising a feed arrangement adapted for, during dialysis treatment, supplying dialysis fluid to a dialyzer; ii) circulating a disinfectant and/or heated fluid in a fluid loop path comprising a return arrangement adapted for, during dialysis treatment, receiving used dialysis fluid from a dialyzer; iii) leading disinfectant and/or heated fluid in the auxiliary fluid loop path towards waste bag or drain, thereby discontinuing the disinfection of the auxiliary fluid loop path, while continuing circulating disinfectant and/or heated fluid in the fluid loop path; iv) commencing the preparation of dialysis fluid in the feed arrangement while continuing circulating disinfectant and/or heated fluid in the fluid loop path.

In a 31$^{st}$ depending aspect according to the previous two method aspects, it is provided the step of re-circulating the disinfectant and/or heated fluid provided in the feed arrangement in an auxiliary fluid loop path, said auxiliary fluid loop path comprising at least a portion of the feed arrangement.

In a 32$^{nd}$ depending aspect according to the previous three method aspects, the following steps are provided: vi) providing a fluid path from the fluid loop path to waste bag or drain; vii) leading disinfectant and/or heated fluid in the fluid loop path towards waste bag or drain, thereby discontinuing the disinfection of the fluid loop path; viii) flowing the dialysis fluid being prepared in the feed arrangement through at least a part of the fluid loop path, now connected to waste bag or drain, and further towards waste bag or drain.

In a 33$^{rd}$ depending aspect according to the previous four method aspects, to the extent such dialysis machine comprises a heat-exchanger between fluid of the auxiliary fluid loop path and fluid of the fluid loop path, the method further comprises the step of: preventing heat transfer between fluid of the fluid loop path and fluid of the auxiliary fluid loop path when dialysis fluid is being prepared and disinfection of the fluid loop path occurs at the same time by short-cutting the primary and/or secondary side of the heat-exchanger.

In a 34$^{th}$ depending aspect according to the previous five method aspects, it is further provided the step of connecting a removable connector of the feed arrangement to the feed recirculation circuit to define the auxiliary fluid loop path and/or connecting a removable connector of the return arrangement to the return recirculation circuit to define the fluid loop path.

In a 35$^{th}$ depending aspect according to the previous six method aspects, it is further provided the step of filling with purified water the feed arrangement, and particularly the auxiliary fluid loop path, and the fluid loop path and heating purified water in the feed arrangement and/or in the fluid loop path.

In a 36$^{th}$ depending aspect according to the previous aspect, heating of the purified water in the feed arrangement is independent from heating in the fluid loop path.

In a 37$^{th}$ depending aspect according to the previous two aspects, a disinfectant is added to purified water in the feed arrangement and/or in the fluid loop path.

In a 38$^{th}$ depending aspect according to the previous eight method aspects, anyone of the steps of providing a disinfectant and/or heated fluid, re-circulating a disinfectant and/or heated fluid, leading disinfectant and/or heated fluid towards waste bag or drain, circulating a disinfectant and/or heated fluid, commencing the preparation of dialysis fluid, flowing the dialysis fluid, preventing heat transfer, filling with purified water, heating purified water is performed by a controller, in particular a controller of the dialysis machine.

An advantage, at least in respect of some embodiments of the present invention, is that time between treatments can be reduced thereby allowing a higher number of treatments in the clinic or longer treatment for the patient.

Another advantage, at least in respect of some embodiments of the present invention, is that disinfection of the auxiliary fluid loop path (clean side upstream the dialyzer) and of the fluid loop path (dirty side downstream the dialyzer) are independent one another; short heating cycles (e.g. 5 minutes) may be adopted in the auxiliary fluid loop path disinfection independently from the fluid loop path disinfection occurrence or timing.

Another advantage, at least in respect of some embodiments of the present invention, is that when performing the short heating cycle followed by the preparation of the treatment fluid in the auxiliary fluid loop path in parallel with the longer heating cycle in the fluid loop path, the time between treatments can be shortened (e.g. approximately 10 minutes).

DETAILED DESCRIPTION

Figure 1:
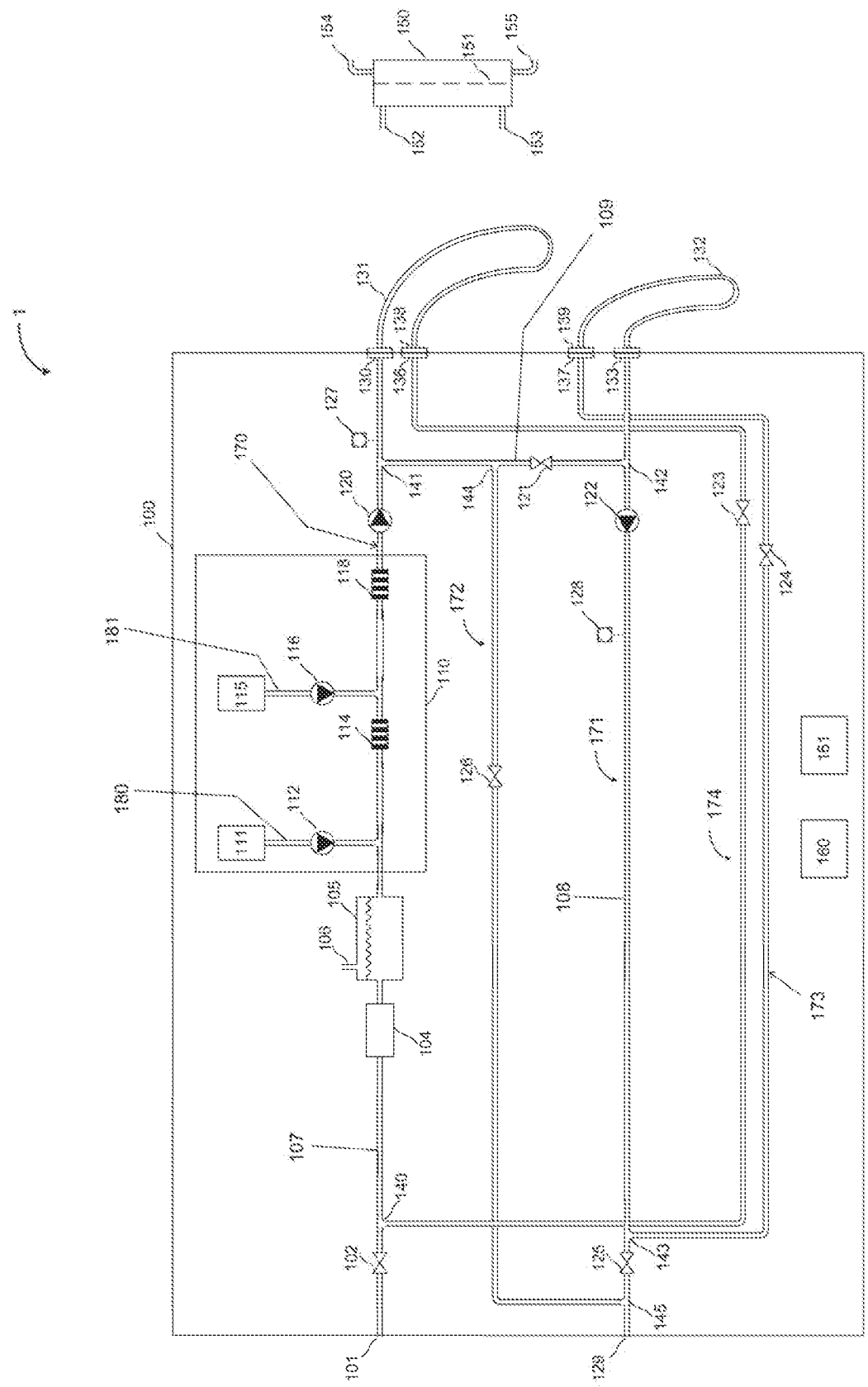
FIG. 1 shows a schematic diagram of a portion of a dialysis machine according to an embodiment of the present invention.

FIG. 1 shows a schematic diagram of a portion of a dialysis machine 1 according to an embodiment of the present invention.

Various alternative examples of a dialysis machine 1 including variants of the hydraulic circuit 100; 200; 300; 400; 500; 600 are schematically illustrated in FIGS. 1 to 6, but it is to be noted that other and different circuits to those specifically shown in the figures might be used in consequence of the functional and design needs of the dialysis machine 1. Moreover, throughout the present description, identical components are identified with the same reference numbers in the various drawings.

In the following description, if not explicitly specified, the terms 'upstream' and downstream' are referred to the usual fluid flow direction of the circulating fluid in the referred tubing/lines.

Firstly, a general description of the dialysis machine 1 and of its hydraulic circuit is provided in respect to the embodiment of FIG. 1; possible other embodiments are thereafter described with respect to FIGS. 2 to 6 with respect to the included variations, only.

According to the example of FIG. 1, the dialysis machine 1 has a hydraulic circuit 100 exhibiting a feed arrangement 170 presenting at least one dialysis supply line 107 generally destined to transport a fluid from an inlet 101 towards a dialyzer 150 during a dialysis treatment.

The hydraulic circuit 100 further comprises a return arrangement 171 having at least one dialysis effluent line 108, destined for the transport of a dialysate liquid (spent dialysate and/or liquid ultrafiltered from the blood through a semipermeable membrane 151 of the dialyzer 150) from the dialyzer 150 towards an exit, schematically denoted by 129 in FIG. 1.

The hydraulic circuit 100 cooperates with a blood circuit (not represented). The specific structure of the blood circuit is not fundamental, with reference to the present invention. Thus, simply a brief description of a possible embodiment of a blood circuit is made, which is however provided purely by way of non-limiting example.

The blood circuit comprises a blood withdrawal line designed to remove blood from a vascular access and a blood return line designed to return the treated blood to the vascular access.

The blood circuit further comprises a primary chamber, or blood chamber, of the dialyzer 150, the secondary chamber of which is connected to the hydraulic circuit 100.

In greater detail, the blood withdrawal line is connected at the dialyzer blood fluid inlet 155 of the primary chamber, while the blood return line is connected at the dialyzer blood fluid outlet 154 of the primary chamber.

In turn, during a dialysis treatment, the dialysis supply line 107 is connected at the dialyzer treatment fluid inlet 152 of the secondary chamber, while the dialysis effluent line 108 is connected at the dialyzer treatment fluid outlet 153 of the secondary chamber.

The dialyzer 150, for example a dialyzer or a plasma filter or a hemofilter or a hemodiafilter, comprises, as mentioned, the two chambers and which are separated by a semipermeable membrane 151, for example of the hollow-fibre type or plate type.

The blood circuit may also comprise one or more air separators, e.g. in the blood return line, upstream of a safety valve. Other air separators may be present in the blood circuit, such as positioned along the blood withdrawal line.

The dialysis machine 1 may also comprise one or more blood pumps, for example positive displacement pumps such as peristaltic pumps, e.g. on the blood withdrawal line.

With the aim of controlling the fluid passage towards/from the dialyzer 150, a flow pump 120 and a suction pump 122 may be included, located respectively on the dialysis fluid supply line 107 and on the dialysate effluent line 108 and also operatively connected to a controller 160 of the dialysis machine 1.

When preparing a fluid for treating a patient, purified water enters into the feed arrangement at inlet 101. An inlet valve 102 is open and the water is heated at the desired temperature (e.g. 37°) by means of a heater 104.

Purified and heated water is collected into a tank 105 provided with an expansion tube 106 to allow gases, eventually dissolved in the liquid, to be released to the atmosphere.

The apparatus also comprises a treatment fluid preparation unit 110 which may be of any known type, for example including one or more concentrate containers (A-concentrate 111 and B-concentrate 115) and respective concentrate pumps (A-pump 112 and B-pump 116) for the concentrate delivery, as well as at least a first and/or a second conductivity cell 114, 118.

Concentrate pump/s 112, 116 is/are arranged in the delivery line/s 180, 181 in order to allow the metered mixing of water and concentrated solution in the dialysis supply line 107. The concentrate pump/s 112, 116 is/are driven on the basis of the comparison between 1) a target conductivity value for the mixture of liquids formed at respective infusion points where the dialysis supply line 107 joins the delivery line/s 180, 181, and 2) the value of the conductivity of this mixture measured by means of a respective conductivity sensor 114; 118 arranged in the dialysis supply line 107 downstream of the infusion point between the dialysis supply line 107 and the respective delivery line/s 180; 181.

In particular, the first concentrate may be mixed with purified water in the dialysis supply line and the fluid conductivity measured immediately downstream the first infusion point. The second infusion point may be placed downstream the first conductivity cell 114 and the second concentrate mixes with the fluid in the dialysis supply line. Conductivity of the prepared treatment fluid may be thereafter measured with the second conductivity cell 118 before being directed to the dialyzer 150 for the treatment.

The dialysis fluid may contain, for example, ions of sodium, calcium, magnesium and potassium and the treatment fluid preparation unit 110 may be configured to prepare the dialysis fluid on the basis of a comparison between a target conductivity value and an actual conductivity value of the dialysis fluid measured by the conductivity sensors 114, 118.

The concentrate pump/s 112, 116 is/are generally configured to control the concentration of specific ionic substances in the dialysis liquid. Generally it is advantageous to control the sodium and bicarbonate concentration of the dialysis fluid.

Figure 2:
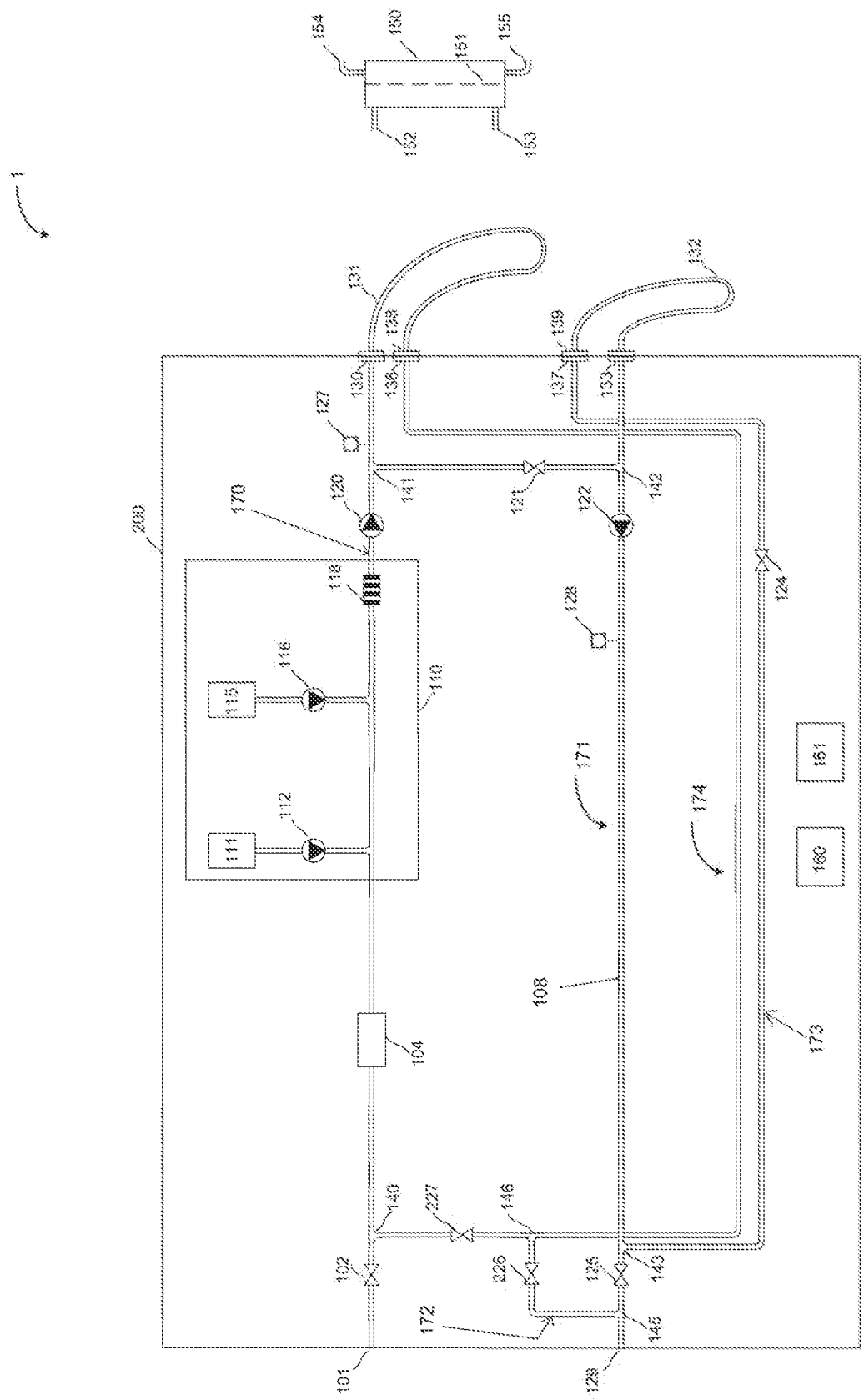
FIG. 2 shows a schematic diagram of a portion of a dialysis machine according to an alternative embodiment of the present invention.

In the example of FIG. 2, only one conductivity sensor 118 is used to control dialysis fluid preparation. The conductivity sensor 118 is placed on the feed arrangement downstream the infusion points of the first and second concentrate.

Of course other kinds of treatment fluid preparation unit 110 might be equivalently used, having a single or further concentrate sources and/or a single or more pumps. Indeed, the treatment fluid preparation unit 110 may be any known system configured for on-line preparing dialysis fluid from water and concentrates. The treatment fluid preparation unit 110 may be, for example, the one described in the U.S. Pat. No. 6,123,847 the content of which is herein incorporated by reference.

Since the dialysis apparatus may comprise various liquid sources (for example one or more water sources, one or more concentrate sources 111, 115, one or more sources of disinfectant liquids) connected to the dialysis supply line 107 with respective delivery lines, the apparatus may exhibit, at each delivery line, a respective check member (not all are shown), for example, comprising the mentioned inlet valve 102 for enabling and preventing, respectively, purified water from the inlet 101 to be lead to the treatment fluid preparation unit 110 through said feed forward arrangement 170.

As shown, the dialysis supply line 107, whose upstream inlet 102 is intended to be connected to a source of running water, also connects the treatment fluid preparation unit 110 for preparing dialysis fluid to the dialyzer 150.

Arranged in this dialysis supply line 107, in the direction in which the fluid circulates, there are the first flow meter (not shown), the flow pump 120 and a first fluid path temperature sensor 127 to check temperature of the fluid in the feed arrangement 170.

The treatment fluid outlet 130 of the dialysis supply line 107 may be connected to a treatment fluid removable connector 138 which is configured to be connected to the dialyzer treatment fluid inlet 152 when treating a patient.

When disinfecting the feed arrangement 170, a disinfectant and/or a heated fluid are circulated in the dialysis supply line 107.

In particular, the treatment fluid removable connector 138 of the dialysis supply line 107 is disconnected from the dialyzer 150 and is connected to a supply tube parking connector 136 provided in the chassis of the dialysis machine. A feed recirculation circuit 174 is designed to receive fluid from the supply tube parking connector 136 and to direct said fluid again to the feed arrangement 170, in particular to the dialysis supply line 107 at a first connection point 140 immediately downstream the inlet valve 102. With such a tubing configuration, an auxiliary fluid loop path is defined allowing fluid re-circulation in said closed loop path including, at least a portion of, the feed arrangement 170 and the feed recirculation circuit 174.

In case of heat disinfection only, water is fed through the inlet 101 and heated to the desired disinfection temperature by heater 104. For example water at a temperature of 70°-95° degrees may be used. The flow pump 120 operates continuously pumping the fluid in the auxiliary fluid loop path. Heated water passes along the feed arrangement 170, the treatment fluid outlet 130, a treatment fluid supply tube 131, the supply tube parking connector 136 and the feed recirculation circuit 174 back to the feed arrangement 170. In other terms, heated water is re-circulated in the closed auxiliary fluid loop path for a predetermined time period, e.g. 5 minutes, sufficient to perform heat disinfection of the portion of the hydraulic circuit upstream the dialyzer 150.

A first return valve 123 is placed in the feed recirculation circuit 174 for enabling and preventing, respectively, the circulation of fluid in the auxiliary fluid loop path. The first return valve 123 is open during heat disinfection.

Notably, disinfection may alternatively be obtained using a disinfectant mixed with water; disinfection may be achieved combined with heating of the disinfectant solution or not.

A return arrangement 171 is arranged to remove the dialysis fluid from the dialyzer 150 during dialysis treatment and forward it to the exit 129. The dialysis effluent line 108 may be provided with a respective return fluid removable connector 139 to be removably connected to the dialyzer treatment fluid outlet 153 when treating a patient to receive dialysate fluid and directing it towards the exit 129. The exit is adapted for connection to a waste-bag or to a drain.

A suction pump 122 and a second flow meter (not shown) are disposed on the dialysis effluent line 108. The first and second flow meters may be used to control (in a known manner) the fluid balance of a patient connected to the blood circuit during a dialysis treatment session.

A conductivity sensor, not shown, is provided on the dialysis effluent line 108, immediately downstream the dialyzer 150, to measure conductivity of the dialysate.

Additionally, a second fluid path temperature sensor 128 is placed downstream the suction pump 122 to measure the temperature of the fluid circulating in the return arrangement 171.

A first exit valve 125 is placed in the return arrangement 171 immediately upstream the exit 129 for enabling and preventing, respectively, fluid of the return arrangement to be lead to the exit.

When disinfecting the return arrangement 171, a disinfectant and/or a heated fluid are circulated in the dialysis effluent line 108.

In particular, the return fluid removable connector 139 of the dialysis effluent line 108 is disconnected from the dialyzer 150 and is connected to a return tube parking connector 137 provided in the chassis of the dialysis machine. A return recirculation circuit 173 is designed to receive fluid from the return tube parking connector 137 and to direct said fluid again to the return arrangement 171, in particular to the dialysis effluent line 108 at a fourth connection point 143 immediately upstream the first exit valve 125 and the exit 129. With such a tubing configuration, a fluid loop path is defined allowing fluid re-circulation in a closed loop path including, at least a portion of, the return arrangement 171 and the return recirculation circuit 173.

In an embodiment (not shown), only the fluid loop path is present to recirculate fluid, particularly during disinfection; the auxiliary fluid loop path not being present in the 'clean side' of the hydraulic circuit. In this embodiment, no feed recirculation circuit is provided.

In case of heat disinfection only, hot water, heated to the desired disinfection temperature e.g. by heater 104, is fed to the fluid loop path through the feed arrangement 170. For example water at a temperature of 70°-95° degrees may be used.

It is noted that hot water may be provided via a by-pass line 109 or any other fluid connection between the dialysis supply line 107 (including the heater 104) and the fluid loop path.

Alternatively, or in combination, an additional heater may be provided in the return arrangement 171 or in the return recirculation circuit 173, to heat water.

In another embodiment, a heat exchanger may be used to transfer heat from the fluid in the feed arrangement 170 to the fluid in the return arrangement 171 to reach the desired temperature of the fluid in the fluid loop path. Additional heater in the return arrangement may or may not be present.

The suction pump 122 operates continuously pumping the fluid in the fluid loop path. Heated water passes through the return arrangement 171, the return recirculation circuit 173, the return tube parking connector 137, a treatment fluid return tube 132, a treatment fluid return inlet 133, and back to the return arrangement 171. In other terms, heated water is re-circulated in the closed fluid loop path for a predetermined time period, e.g. 15 minutes, sufficient to perform heat disinfection of the portion of the hydraulic circuit downstream the dialyzer 150.

A second return valve 124 is placed in the return recirculation circuit 173 for enabling and preventing, respectively, the circulation of fluid in the fluid loop path. The second return valve 124 is open during heat disinfection.

Notably, disinfection of the fluid loop path may alternatively be obtained using a disinfectant mixed with water; disinfection may be achieved combined with heating of the disinfectant solution or not.

The hydraulic circuit 100 according to FIG. 1 also includes a feed forward arrangement 172 arranged to enable a fluid of the feed arrangement 170 to be forwarded to a waste bag or drain by-passing the fluid loop path, i.e. by-passing the portion of the return arrangement 171 upstream the first exit valve 125 and by-passing the return recirculation circuit 173.

In the embodiment of FIG. 1, the feed forward arrangement 172 is directly connected to the exit 129 of the return arrangement 171. However, it is noted that the feed forward arrangement 172 may be directly connected to the drain (or waste-bag) without being connected to the return arrangement 171. In other terms, the feed forward arrangement 172 may, in some embodiments, have a discharge end portion independent and not directly connected to other lines of the hydraulic circuit and freely placeable.

The feed forward arrangement 172 of FIG. 1 is connected to the auxiliary fluid loop path (in particular to the feed arrangement 170) at a second connection point 141. Fluid from the auxiliary fluid loop path may be withdrawn at the second connection point 141 and directed to the exit 129 without circulating in the fluid loop path before being discharged. In particular, in the examples, the feed forward arrangement 172 is connected to the return arrangement 171 at a sixth connecting point 145 placed downstream the fourth connecting point 143 where the return recirculation circuit 174 connects to the return arrangement 171.

The feed forward arrangement 172 comprises a second exit valve 126 for enabling and preventing, respectively, fluid of the feed arrangement to be lead to the exit through said feed forward arrangement.

The hydraulic circuit 100 may also comprise a bypass line 109 which connects the dialysis fluid supply line 107 and the dialysate effluent line 108 bypassing the dialyzer 150, and one or more bypass valves 121 connected to the controller 160 for selectively opening and closing the bypass line 109. The bypass valve 121 on command of the controller opens; further the controller 160 closes the fluid passage towards the treatment zone and connect the inlet 101 directly with the dialysis effluent line 108 through the bypass line 109.

In the example of FIG. 1, a first tract of the by-pass line between the second connection point 141 and a fifth connection point 144 is in common with the feed forward arrangement 172. In other terms, by properly controlling opening/closure of the bypass valve 121 and of the second exit valve 126 it is possible to direct fluid from the feed arrangement 170 either towards the return arrangement 171 or towards the exit 129. In addition, both bypass valve 121 and second exit valve 126 may be open at the same time whereby it is possible to direct fluid from the feed arrangement 170 both towards the return arrangement 171 and towards the exit 129. The by-pass line 109 is connected to the return arrangement 171 at a third connection point 142, upstream the suction pump 122.

The apparatus of above-described embodiment may also comprise a user interface 161 (e.g. a graphic user interface or GUI) and a controller 160, i.e. a programmed/programmable controller, connected to the user interface.

The controller 160 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

The controller 160 of the dialysis apparatus represented in FIG. 1 may be connected to the (graphic) user interface 161 through which it may receive instructions, for example target values, such as blood flow rate Qb, dialysis fluid flow rate Qdi, infusion liquid flow rate Qinf (where appropriate), patient weight loss WL. The controller 160 furthermore may receive detected values by the sensors of the apparatus, such as the aforementioned flow meters, the conductivity sensors of treatment fluid preparation unit 110 and the conductivity sensor in the dialysis effluent line 108 and the first and second fluid path temperature sensors 127, 128. On the basis of the instructions received and the operating modes and algorithms which have been programmed, the controller 160 drives the actuators of the apparatus, such as the blood pump, the aforementioned flow and suction pumps 120, 122, and the treatment fluid preparation unit 110. Of course, the controller 160 may present information to the user (e.g. treatment parameters and machine parameters) by means of the (graphic) user interface 161.

FIG. 2 describes a second embodiment for a hydraulic circuit 200 in a dialysis machine 1. The hydraulic circuit 200 according to the second embodiment slightly differs from the hydraulic circuit of FIG. 1.

In more detail, the feed forward arrangement 172 is directly connected to the auxiliary fluid loop path at a seventh connection point 146. In particular, the seventh connection point 146 is placed along a direction of fluid recirculation in the auxiliary fluid loop path and upstream a fourth exit valve 227.

The feed forward arrangement 172 of FIG. 2 also includes a respective third exit valve 226 for enabling and preventing, respectively, fluid of the feed arrangement 172 to be lead to the exit through said feed forward arrangement.

By suitably driving opening and closing of said first return valve 123, said third exit valve 226 and said fourth exit valve 227, it is possible to either re-circulate the fluid in the auxiliary fluid loop path or direct the fluid of the feed arrangement to the exit 129.

Figure 3:
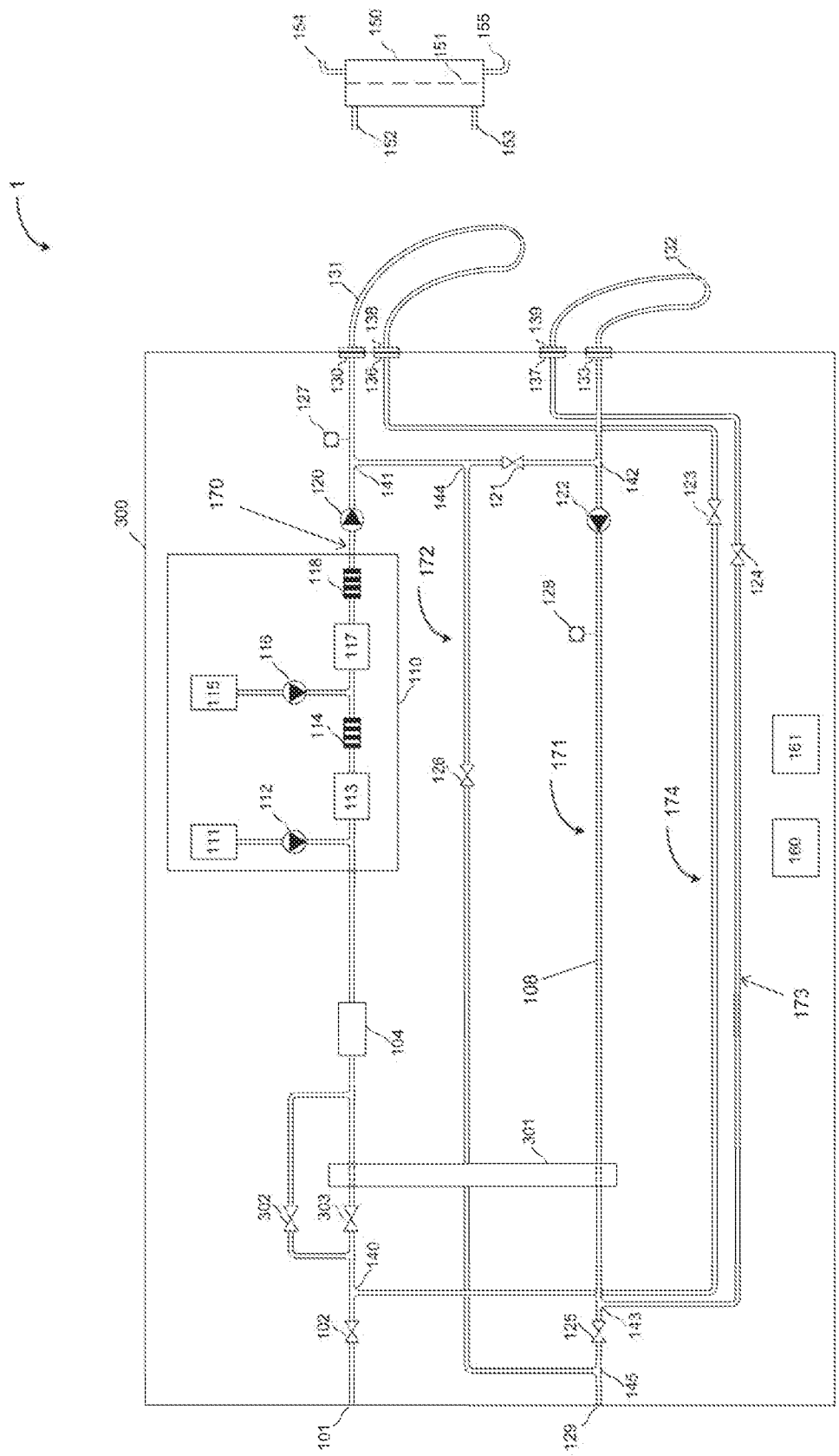
FIG. 3 shows a schematic diagram of a portion of a dialysis machine according to a further alternative embodiment of the present invention.
Figure 4:
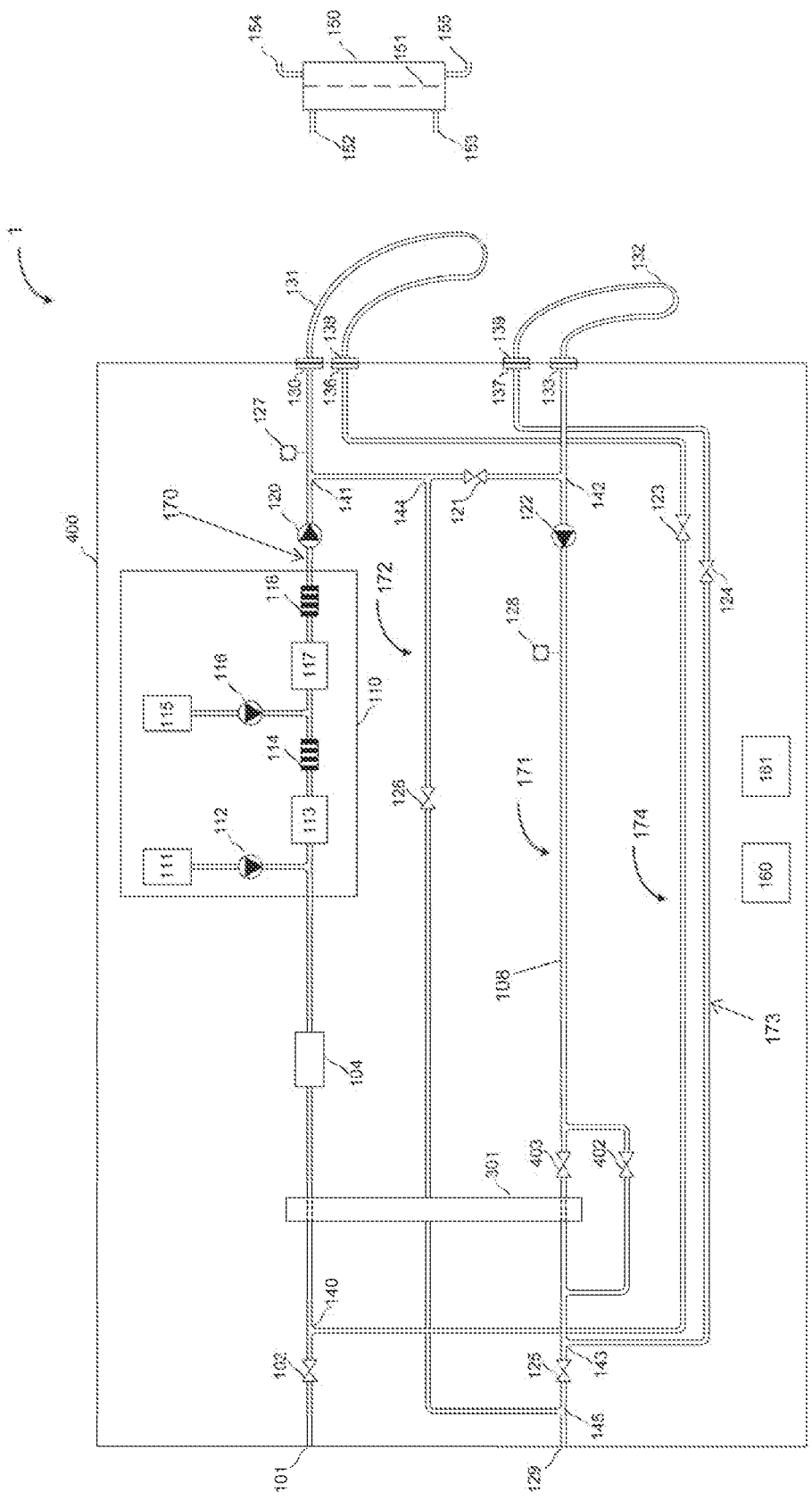
FIG. 4 shows a schematic diagram of a portion of a dialysis machine according to a further alternative embodiment of the present invention.
Figure 5:
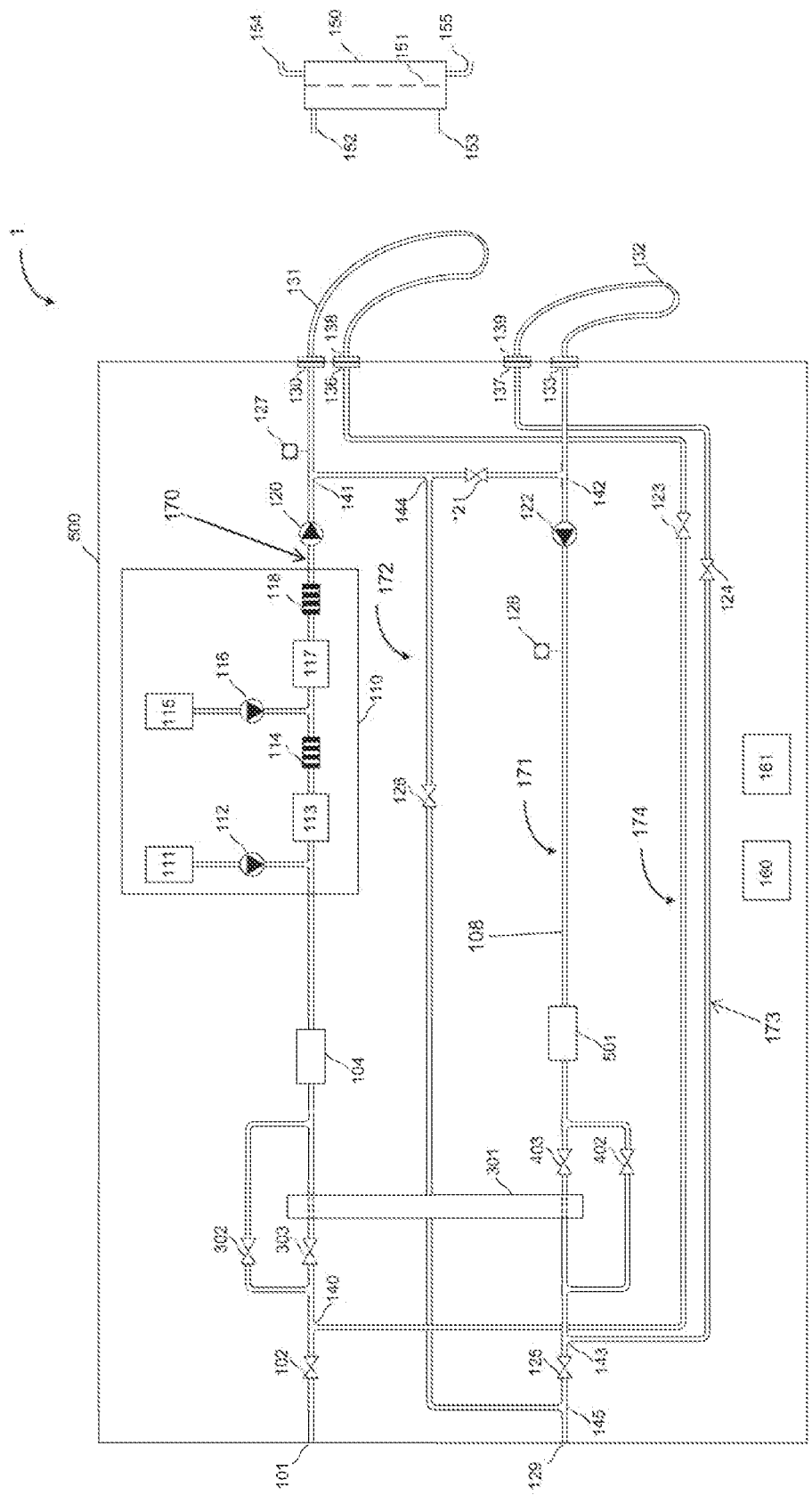
FIG. 5 shows a schematic diagram of a portion of a dialysis machine according to a further alternative embodiment of the present invention.

FIGS. 3, 4 and 5 describe respectively a third, a fourth and a fifth embodiment for a hydraulic circuit 300; 400; 500 in a dialysis machine 1.

In more detail, the treatment fluid preparation unit 110 may include two mixing chambers 113, 118. The first concentrate may be mixed with purified water in a first mixing chamber 113 and the fluid conductivity measured immediately downstream the first mixing chamber 113. The second infusion point may be placed downstream the first conductivity cell 114 and the second concentrate mixes with the fluid in the dialysis supply line at a second mixing chamber 117. Conductivity of the prepared treatment fluid may be thereafter measured with the second conductivity cell 118 before being directed to the dialyzer 150 for the treatment. It is noted that mixing chambers 113, 117 may or may not be present in the feed arrangement 170.

Additionally, the hydraulic circuit includes a heat exchanger 301 with a primary and a secondary side; the primary side is connected to the feed arrangement 170, e.g. to the dialysis supply line 107, the secondary side is connected to the return arrangement 171, e.g. to the dialysis effluent line 108.

The heat exchanger 301 is arranged to transfer heat between a fluid circulating in the feed arrangement and a fluid circulating in the fluid loop path.

At least one short-cut arrangement is arranged to short-cut the primary and/or the secondary side of the heat-exchanger 301.

FIG. 3 shows an embodiment with a short cut in the primary side, only; a first heat exchanger by-pass line is provided to by-pass the primary side. The first heat exchanger by-pass line includes a first heat exchanger short-cut valve 302 for enabling and preventing, respectively, the circulation of fluid in the first heat exchanger by-pass line.

A second heat exchanger short-cut valve 303 is provided in the feed arrangement 170 upstream the heat exchanger 301 and downstream a withdrawal point for connection to the first heat exchanger by-pass line.

By suitably driving opening and closing of said first heat exchanger short-cut valve 302 and said second heat exchanger short-cut valve 303, it is possible to either circulate the fluid in the heat exchanger 301 or short cut the primary side of the same heat exchanger 301.

FIG. 4 shows an embodiment with a short cut in the secondary side, only; a second heat exchanger by-pass line is provided to by-pass the secondary side. The second heat exchanger by-pass line includes a third heat exchanger short-cut valve 402 for enabling and preventing, respectively, the circulation of fluid in the second heat exchanger by-pass line.

A fourth heat exchanger short-cut valve 403 is provided in the return arrangement 171 upstream the heat exchanger 301 and downstream a withdrawal point for connection to the second heat exchanger by-pass line.

By suitably driving opening and closing of said third heat exchanger short-cut valve 402 and said fourth heat exchanger short-cut valve 403, it is possible to either circulate the fluid in the heat exchanger 301 or short cut the secondary side of the same heat exchanger 301.

FIG. 5 shows an embodiment of hydraulic circuit 500 with a short cut both in the primary side and in the secondary side of the heat exchanger 301.

A second heater 501 is provided in the return arrangement 171, in particular downstream the suction pump 122 and upstream the heat exchanger 301.

Figure 6:
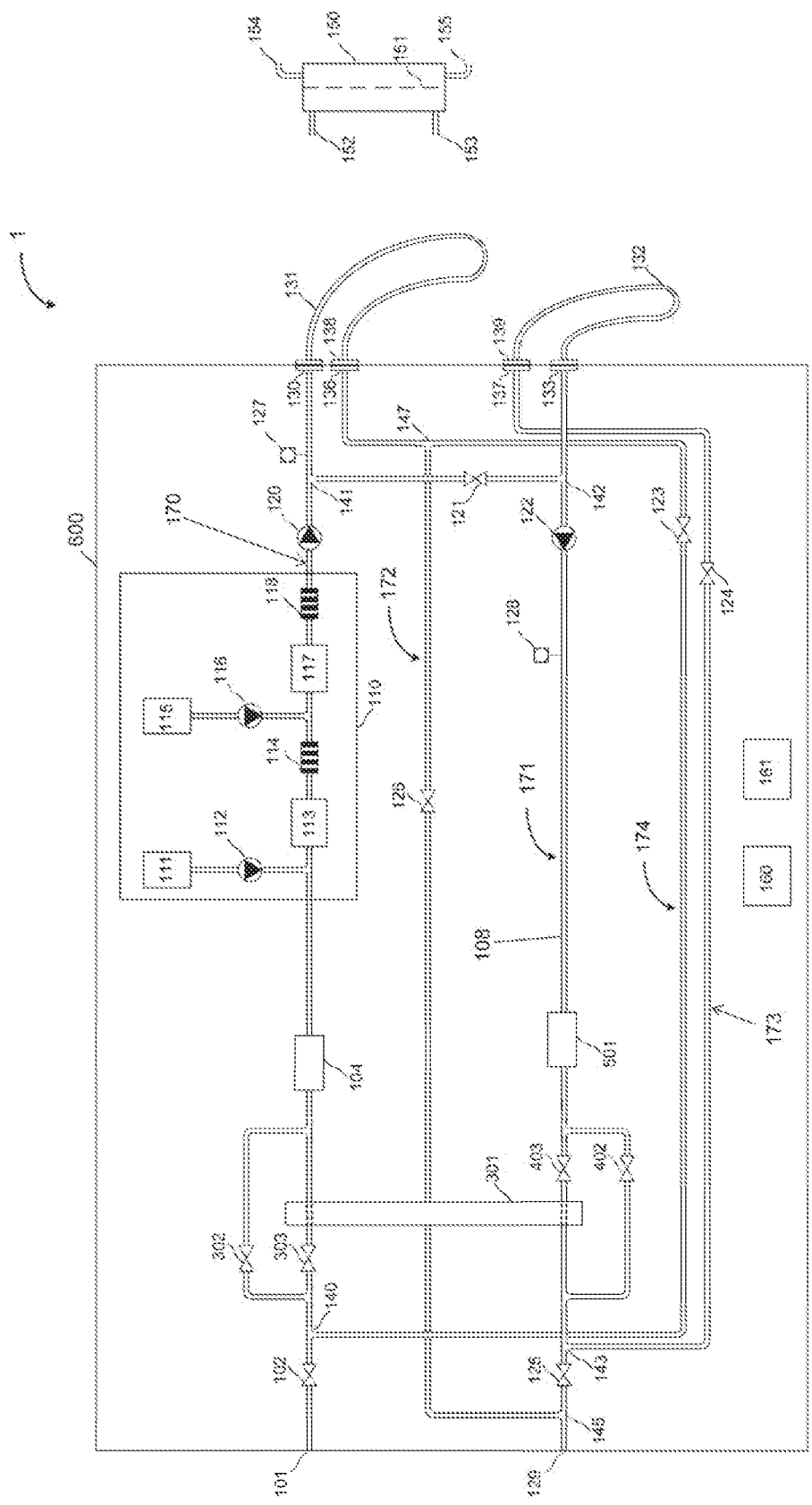
FIG. 6 shows a schematic diagram of a portion of a dialysis machine according to a further alternative embodiment of the present invention.

FIG. 6 illustrates a hydraulic circuit 600 including the heat exchanger 301 and the respective short-cuts, as well as a heater 501 in the return arrangement 171.

Additionally, the feed forward arrangement 172 of FIG. 6 is connected to the auxiliary fluid loop path at an eight connection point 147 which is placed on the return arrangement 171 upstream the first return valve and downstream the supply tube parking connector 136.

As already mentioned, the described embodiments are intended to be non-limiting examples. In particular the hydraulic circuits of FIGS. 1 to 6 should not be interpreted as defining or limiting, as they may comprise other additional or alternative components to those described.

For example an ultrafiltration line may be included, with at least one respective pump connected to the dialysis effluent line 108.

Furthermore one or more devices for measuring specific substance concentrations might be implemented either (or both) in the feed arrangement 170 or (and) in the return arrangement 171 of the hydraulic circuit. Concentration of calcium, potassium, magnesium, bicarbonate, and/or sodium might be desired to be known.

Finally, the above-cited one or more pumps and all the other necessary temperature, pressure and concentration sensors may operate either on the dialysis supply line 107 and/or on the dialysis effluent line 108, in order to adequately monitor the preparation and movement of the liquid in the hydraulic circuit.

Given the above description of the circuit, the dialysis machine can operate according to the following operating modes.

In a disinfection mode, in order to prevent growth of microorganisms in the feed arrangement 170, e.g. during the day, the auxiliary fluid loop path (i.e. a portion of the feed arrangement 170 and the feed recirculation circuit 174) is subjected to the re-circulation of heated water (and/or disinfectant) during a short period of time (e.g. 5 minutes at less than 80 degrees Celsius) in between treatments. The return arrangement 171, which may additionally be contaminated by microorganisms and blood borne virus, may be subjected to the re-circulation of heated water (particularly at higher temperature) in the fluid loop path (i.e. a portion of the return arrangement 171 and the return recirculation circuit 173) during a longer period of time (e.g. 15 minutes at 80-90 degrees Celsius) in between treatments.

Alternatively, in disinfection mode to prevent growth of microorganisms in the feed arrangement 170, heated water (and/or disinfectant) during a short period of time may be circulated in the feed arrangement 170, i.e. the auxiliary fluid loop path may not be present (or not subjected to heated water or disinfectant flow), while the return arrangement 171 may be subjected to the re-circulation of heated water (particularly at higher temperature) or disinfectant in the fluid loop path. In this latter situation, heated water or disinfectant circulates (and is not re-circulated) in the feed arrangement 170 being e.g. directly discharged through the feed forward arrangement 172. Therefore, the feed arrangement 170 is disinfected for a short time without recirculation, and the disinfection of the return arrangement 171 is then continued by re-circulation while the dialysis fluid for the treatment is being prepared.

Additionally, the short heating cycle (e.g. 5 minutes) in the feed arrangement 170 may be combined with a subsequent dialysis fluid preparation cycle. The dialysis fluid preparation cycle, which may take e.g. 10 minutes, includes the starting up of dialysis fluid production in the feed arrangement 170.

At the same time, i.e. during the short heating cycle in the feed arrangement 170 and during the following dialysis fluid preparation cycle (which together may take approximately 15 minutes), the return arrangement may additionally be subjected to the longer circulation of heated water and/or disinfectant (which also takes approximately 15 minutes).

When performing the short heating cycle followed by the dialysis fluid preparation cycle in the feed arrangement 170 in parallel with the longer heating cycle in the return arrangement, the time between treatments can be shortened (e.g. of about 10 minutes).

The time between treatments is also shortened when only the feed arrangement 170 is disinfected by a short heating cycle between the treatments (that is, without disinfection of the return arrangement 171). A full disinfection of the entire hydraulic circuit is then performed on a regular basis (e.g. on a daily basis).

In more detail, during disinfection in between treatments, the treatment fluid removable connector 138 is disconnected from the dialyzer treatment fluid inlet line 152 and connected to the supply tube parking connector 136 (as per in the enclosed figures). Similarly, the return fluid removable connector 139 is disconnected from the dialyzer treatment fluid outlet 153 and connected to the return tube parking connector 137. The fluid loop path and the auxiliary fluid loop path are filled with water coming from inlet 101. Circulations in the fluid loop path and the auxiliary fluid loop path, respectively, are made possible by opening the second return valve 124 and the first return valve 123.

Water in the feed arrangement 170 (and in the auxiliary fluid loop path) is heated by the heater 104 and the water in the return arrangement 171 (and in the fluid loop path) is heated by either the heater 501 in the return arrangement 171 (if present) or the heater 104 in the feed arrangement (and then heat transferred to the return arrangement directly transferring fluid or indirectly transferring heat via the heat exchanger 301). The by-pass valve 121 is closed during disinfection in order to prevent fluid from the fluid loop path to reach the auxiliary fluid loop path. Water and/or disinfectant in the auxiliary fluid loop path is re-circulated by means of the flow pump 120, whereas the water and/or disinfectant in the fluid loop path is re-circulated by means of the suction pump 122. In a first phase, when both the feed and the return arrangements 170, 171 are subjected to respective and independent re-circulation of heated water, the second exit valve 126 (or third exit valve 226) is closed and first exit valve 125 is closed as well. Furthermore, the controller 160 receives signals from the first and second fluid path temperature sensors 127, 128 and controls the respective short-cuts on the heat exchanger 310 (if present) in order to enable the heat to distribute between the fluid loop path and the auxiliary fluid loop path. In detail, the controller 160 measures the temperatures of the fluid loop path and the auxiliary fluid loop path and controls the heaters 104 and 501 and the bypass valve 121 in order to arrive and maintain the temperature in the auxiliary fluid loop path at a high temperature, but being less than 90 degrees Celsius (e.g. 75 degrees Celsius) referred to as the first operating temperature, and the temperature in the fluid loop path at a higher temperature (e.g. in the range of 80-90 degrees Celsius) referred to as the second operating temperature.

A second phase is commenced when water with the first operating temperature has been circulating for a short period of time (e.g. 5 minutes) in the auxiliary fluid loop path. During this second phase, the dialysis fluid preparation cycle is performed in the feed arrangement 170, while water with the second operating temperature continues to be circulated in the fluid loop path. This is achieved by opening the second exit valve 126, closing the first return valve 123 and starting the preparation of dialysis fluid in a known way prior to a new treatment. The prepared dialysis fluid during the dialysis fluid preparation cycle needs to be discharged to the waste bag or drain. Since disinfection may still be on-going in the fluid loop path, the dialysis fluid is instead lead to waste bag or drain by means of the feed forward arrangement 172 with second exit valve 126 (or third exit valve 226— FIG. 2) open. Furthermore, as the temperature of the prepared dialysis fluid should be kept roughly at body temperature, the incoming water to the treatment fluid preparation unit 110 needs to be shielded from the hot water present in the return arrangement 171. To achieve this task, second heat exchanger short-cut valve 303 and/or fourth heat exchanger short-cut valve 403 are closed (and respective by-pass lines opened) thereby short-cutting the heat exchanger 301 on the primary and/or secondary side.

The second phase is completed when the water with the second operating temperature has been circulating for a longer period of time (e.g. 15 minutes) in the fluid loop path. The first exit valve 125 is then opened and the second return valve 124 is closed which leads to that the heated water of the fluid loop path is pumped out to the waste bag or drain. Thereafter, the by-pass valve 121 is opened and the second exit valve 126 is closed thereby leading dialysis fluid prepared by the treatment fluid preparation unit 110 in the feed arrangement 170 through to the return arrangement 171. The dialysis machine is ready to start the next treatment in a known manner.

In an alternative design only the feed arrangement 170 is disinfected to thereby kill bacteria only in the auxiliary fluid loop path and prohibit any significant growth of bacteria upstream the dialyzer 150 (that is, the bacteria that can reach the dialyzer during treatment). This is achieved by disinfecting only the auxiliary fluid loop path in the same manner as above described in between treatments. In this case, the fluid loop path may be emptied of fluid during the disinfection of the auxiliary fluid loop path or the fluid therein may be kept still or be allowed to flow at a low flow rate in order to reduce the exchange of heat between the fluid loop path and the auxiliary fluid loop path (which may occur for example in the heat exchanger 301—if not short-cut as above discussed). Of course, the return arrangement 171 needs to be disinfected on a regular basis as well (e.g. once a day). However, the amount of bacteria and virus that may grow in between such disinfection of the fluid loop path may be deemed to be on an acceptable low level, since these bacteria and virus will not be able to reach the dialyzer 150 during treatment (as the return arrangement 171 is located downstream of the dialyzer 150).

In addition to the disinfections between treatments as above discussed, the complete hydraulic circuit needs a full disinfection on a regular basis (e.g. once a day). Additionally, the dialysis machine 1 may be provided by a control mechanism/algorithm (in particular implemented using the controller 160) such that the short disinfections of the feed arrangement (auxiliary fluid loop path) can only be repeated a pre-set number of times before a disinfection of the complete hydraulic circuit (fluid loop path and auxiliary fluid loop path) is mandatory required. Alternatively, the control mechanism/algorithm sets a limit to how long accumulated time disinfection at the first operating temperature in the feed arrangement is allowed to be performed, over a set period of time, before disinfection of the complete hydraulic circuit will be required.

The above disinfection steps have been primarily referred to thermal disinfection. Additionally, or alternatively, disinfection agents may be added to heated water (or to water) in any one of the disinfection steps in both the fluid loop path and auxiliary fluid loop path or exclusively in one of the mentioned loop paths.

An advantage, at least in respect of some embodiments of the present invention, is that the time required for disinfection between treatments has been reduced.

Another advantage, at least in respect of some embodiments of the present invention, is that it is possible to independently disinfect the feed arrangement 170 and/or the return arrangement 171.

Another advantage, at least in respect of some embodiments of the present invention, is that it is possible to start preparing treatment fluid at the same time disinfecting a portion of the machine hydraulic circuit.

The invention claimed is:

1. A dialysis machine comprising:
a feed arrangement arranged to supply a dialysis fluid to a dialyzer during dialysis treatment;
a return arrangement arranged to remove spent dialysis fluid from the dialyzer during dialysis treatment and direct the spent dialysis fluid to an outlet adapted for connection to a drain;
a return recirculation circuit connected to the return arrangement, the return recirculation circuit arranged to direct a fluid of the return arrangement to a fluid loop path that includes (i) at least a portion of the return arrangement and (ii) the return recirculation circuit;
a feed forward arrangement arranged to enable a fluid of the feed arrangement to bypass the fluid loop path and be directed to the drain; and
a controller configured to perform disinfection of at least one of the feed arrangement and the return arrangement, wherein the disinfection is performed by circulating at least one of a disinfectant and a heated fluid through the at least one of the feed arrangement and the return arrangement.

2. The dialysis machine according to claim 1, further comprising a feed recirculation circuit connected to the feed arrangement, the feed recirculation circuit arranged to direct the feed arrangement fluid to an auxiliary fluid loop path, the auxiliary fluid loop path including (i) at least a portion of the feed arrangement and (ii) the feed recirculation circuit.

3. The dialysis machine according to claim 2, wherein the feed forward arrangement is connected to the auxiliary fluid loop path and arranged to enable the feed arrangement fluid to bypass the fluid loop path and be directed to the drain.

4. The dialysis machine according to claim 2, wherein the controller is configured to perform disinfection of the feed arrangement by re-circulating the at least one of the disinfectant and the heated fluid through said auxiliary fluid loop path.

5. The dialysis machine according to claim 1, wherein the controller is configured to perform disinfection of the return arrangement by re-circulating the at least one of the disinfectant and the heated fluid through the fluid loop path.

6. The dialysis machine according to claim 1, wherein the controller is configured to direct the feed arrangement fluid to the outlet at the same time as at least a portion of the return arrangement contains a fluid different than the feed arrangement fluid.

7. The dialysis machine according to claim 1, wherein the controller is configured to perform disinfection of the feed arrangement and of the return arrangement separately, by circulating at least one of a first disinfectant and a first heated fluid through at least a portion of the feed arrangement and by re-circulating at least one of a second disinfectant and a second heated fluid through the fluid loop path.

8. The dialysis machine according to claim 7, further comprising a feed recirculation circuit connected to the feed arrangement, the feed recirculation circuit arranged to direct the feed arrangement fluid to an auxiliary fluid loop path, the auxiliary fluid loop path including (i) at least a portion of the feed arrangement and (ii) the feed recirculation circuit, and wherein the controller is configured to perform disinfection of the feed arrangement and of the return arrangement separately, by re-circulating the at least one of the first disinfectant and the first heated fluid through the auxiliary fluid loop path.

9. The dialysis machine according to claim 1, wherein the controller is configured to re-circulate the return arrangement fluid in the fluid loop path at the same time as the feed arrangement fluid is directed from the feed arrangement to the outlet via the feed forward arrangement.

10. The dialysis machine according to claim 1, further comprising a feed recirculation circuit connected to the feed arrangement, the feed recirculation circuit arranged to direct the feed arrangement fluid to an auxiliary fluid loop path, the auxiliary fluid loop path including (i) at least a portion of the feed arrangement and (ii) the feed recirculation circuit, and wherein the controller is configured to re-circulate the return arrangement fluid in the fluid loop path at the same time the feed arrangement fluid is re-circulated in the auxiliary fluid loop path.

11. The dialysis machine according to claim 1, wherein the controller is configured to:
discontinue the disinfection of the feed arrangement and direct at least one of a first disinfectant and a first heated fluid used to disinfect the feed arrangement towards the outlet via the feed forward arrangement; and
initiate the preparation of dialysis fluid in the feed arrangement.

12. The dialysis machine according to claim 1, wherein the controller is configured to:
discontinue the disinfection of the feed arrangement and direct at least one of a first disinfectant and a first heated fluid towards the outlet via the feed forward arrangement; and
initiate the preparation of dialysis fluid in the feed arrangement while disinfecting the return arrangement with at least one of a second disinfectant and a second heated fluid through the return recirculation circuit.

13. The dialysis machine according to claim 1, wherein the feed forward arrangement includes an exit valve for controlling fluid flow of the feed arrangement fluid through the outlet and the feed forward arrangement.

14. The dialysis machine according to claim 1, wherein the return recirculation circuit includes a valve for controlling fluid circulation in the fluid loop path.

15. The dialysis machine according to claim 2, wherein the feed recirculation circuit includes a valve for controlling fluid circulation in the auxiliary fluid loop path.

16. The dialysis machine according to claim 1, further comprising a heater arranged to heat fluid being circulated in at least one of the feed arrangement and the fluid loop path.

17. The dialysis machine according to claim 1, further comprising:
a heat-exchanger having a primary side and a secondary side, the heat exchanger being arranged to transfer heat between a circulating feed arrangement fluid and a fluid of the fluid loop path; and
at least one short-cut arrangement arranged to short-cut the primary side or the secondary side of the heat-exchanger.

18. The dialysis machine according to claim 17, wherein the controller is configured to:
activate the at least one short-cut arrangement, thereby reducing heat-transfer between fluids of the primary side and the secondary side of the heat-exchanger; and initiate preparation of dialysis fluid in the feed arrangement while disinfecting the return arrangement with the at least one of the disinfectant and the heated fluid through the fluid loop path.

19. The dialysis machine according to claim 1, wherein the feed arrangement further includes a bypass line directly connecting the feed arrangement and the return arrangement, the bypass line including a valve for controlling fluid flow through the bypass line.

20. The dialysis machine according to claim 19, wherein the feed forward arrangement is connected to the bypass line.

21. The dialysis machine according to claim 1, further comprising a treatment fluid preparation unit including: (i) a delivery line having one end connected to the feed arrangement, (ii) a pump in fluid communication with the delivery line and (iii) a first concentrate source connected to the delivery line, wherein the controller is configured to, during treatment fluid preparation, drive the pump to infuse a concentrate solution from the first concentrate source into the circulating feed arrangement fluid at an infusion point.

22. The dialysis machine according to the claim 21, wherein the treatment fluid preparation unit further includes (i) a second delivery line having one end connected to the feed arrangement, (ii) a second pump in fluid communication with the second delivery line, (iii) a second concentrate source connected to the second delivery line, wherein the controller is configured to, during treatment fluid preparation, drive the second pump to infuse a second concentrate solution from the second concentrate source into the circulating feed arrangement fluid at a second infusion point, and (iv) a conductivity sensor downstream the second infusion point, wherein the controller is configured to receive a signal from the conductivity sensor and to control the first pump and the second pump at least based on the signal.

23. A method of disinfecting a dialysis machine comprising:
providing at least one of a disinfectant and a heated fluid;
circulating the at least one of the disinfectant and the heated fluid in a feed arrangement adapted to supply dialysis fluid to a dialyzer during dialysis treatment;
re-circulating the at least one of the disinfectant and the heated fluid in a fluid loop path, the fluid loop path including a return arrangement adapted to receive used dialysis fluid from the dialyzer during dialysis treatment;
directing the at least one of the disinfectant and the heated fluid from the feed arrangement to a drain, thereby discontinuing disinfection of the feed arrangement, while continuing to re-circulate the at least one of the disinfectant and the heated fluid in the fluid loop path; and
initiating the preparation of dialysis fluid in the feed arrangement while continuing to re-circulate the at least one of the disinfectant and the heated fluid in the fluid loop path.

24. The method of disinfecting a dialysis machine according to claim 23, further comprising re-circulating the at least one of the disinfectant and the heated fluid in the feed arrangement in an auxiliary fluid loop path, the auxiliary fluid loop path including at least a portion of the feed arrangement.

25. The method of disinfecting a dialysis machine according to claim 23, further comprising:
providing a fluid path from the fluid loop path to a drain;
directing the at least one of the disinfectant and the heated fluid in the fluid loop path towards the drain, thereby discontinuing disinfection of the fluid loop path; and
directing the prepared dialysis fluid through at least a part of the fluid loop path and to the drain.

26. The method of disinfecting a dialysis machine according to claim 23, wherein the dialysis machine includes a heat-exchanger having a primary side and a secondary side, the heat-exchanger being arranged to transfer heat between fluid of the auxiliary fluid loop path and fluid of the fluid loop path, the method further comprising:
short-cutting at least one of the primary side and the secondary side of the heat-exchanger, thereby preventing heat transfer between fluid of the fluid loop path and fluid of the auxiliary fluid loop path when dialysis fluid is being prepared and enabling simultaneous disinfection of the fluid loop path.

* * * * *